(12) United States Patent
Ito et al.

(10) Patent No.: US 6,635,253 B2
(45) Date of Patent: Oct. 21, 2003

(54) COMPOSITION FOR ENHANCING IMMUNOLOGICAL EFFECTS

(75) Inventors: Shinobu Ito, Tokyo (JP); Eiji Ogata, Chiba (JP)

(73) Assignee: Showa Denko Kabushiki Kaisha, Tokyo (JP)

( * ) Notice: Subject to any disclaimer, the term of this patent is extended or adjusted under 35 U.S.C. 154(b) by 136 days.

(21) Appl. No.: 09/794,161

(22) Filed: Feb. 28, 2001

(65) Prior Publication Data

US 2001/0041182 A1 Nov. 15, 2001

Related U.S. Application Data

(60) Provisional application No. 60/253,744, filed on Nov. 29, 2000.

(30) Foreign Application Priority Data

Feb. 29, 2000 (JP) ..................................... P2000-055019

(51) Int. Cl.[7] ...................... A61K 39/38; A61K 39/116; A61K 39/145; A61K 45/00; A61K 47/00
(52) U.S. Cl. ................................ 424/184.1; 424/203.1; 424/204.1; 424/278.1
(58) Field of Search ........................ 552/547; 424/184.1, 424/201.1, 202.1, 204.1, 278.1, 203.1, 206.1, 209.1, 234.1; 119/174

(56) References Cited

U.S. PATENT DOCUMENTS

| | | | | |
|---|---|---|---|---|
| 4,744,989 A | * | 5/1988 | Payne et al. | 424/490 |
| 5,114,957 A | * | 5/1992 | Hendler et al. | 514/356 |
| 5,785,975 A | * | 7/1998 | Parikh | 424/278.1 |
| 5,937,790 A | * | 8/1999 | Ito et al. | 119/174 |

FOREIGN PATENT DOCUMENTS

| | | |
|---|---|---|
| EP | 0 845 216 A1 | 6/1998 |
| EP | 0 875 514 A1 | 11/1998 |
| EP | 0 884 321 A1 | 12/1998 |

OTHER PUBLICATIONS

Dorland's Illustrated Medical Dictionary, 28th edition. Philadelphia: WB Saunders; 1994. p. 98 and 1373.*
Jyonouchi et al. Nutrition and Cancer. 1996; 26 (3): 313–34, abstract only.*
Okotie et al. Poultry Science. 1997; 76 (10): 1337–1341, abstract only.*
Girodon et al. Archives of Internal Medicine. 1999; 159: 748–754.*
"Adjuvant Properties of Different Forms of Vitamin A in Avian Vaccines", Journal of Nutritional Immunology, vol. 3 (4), 1995, pp. 63–69.
"Vitamin E, Immune Response, and Disease Resistance", Annals of the New York Academy of Sciences, 1989, vol. 570, pp. 335–344.
"The Role of Vitamin E in Immune Response and Disease Resistance", Annals of the New York Academy of Sciences, 1990, vol. 587, pp. 24–33.

* cited by examiner

*Primary Examiner*—James Housel
*Assistant Examiner*—Shanon Foley
(74) *Attorney, Agent, or Firm*—Sughrue Mion, PLLC

(57) ABSTRACT

An object of the present invention is to provide a composition for enhancing the immunological effects of a vaccine for viruses, bacteria and/or infectious disease pathogens, containing a stable activity-type provitamin; a method for enhancing the immunological effects of a vaccine for viruses, bacteria and/or infectious disease pathogens by administering the composition; and a method of employing the composition. A composition for enhancing the immunological effects of a vaccine for viruses, bacteria and/or infectious disease pathogens, contains L-ascorbic acid-2-phosphate and/or α-tocopheryl phosphate as a stable activity antioxidant provitamin.

16 Claims, No Drawings

COMPOSITION FOR ENHANCING IMMUNOLOGICAL EFFECTS

CROSS REFERENCE TO RELATED APPLICATIONS

This application is an application filed under 35 U.S.C. §111(a) claiming benefit pursuant to 35 U.S.C. §119(e)(1) of the filing date of Provisional Application No. 60/253,744 filed Nov. 29, 2000 pursuant to 35 U.S.C. §111(b).

FIELD OF THE INVENTION

The present invention relates to a composition for enhancing the immunological effects of a vaccine for viruses, bacteria and/or infectious disease pathogens, containing "a stable activity provitamin such as an L-ascorbic acid-2-phosphate and/or α-tocopheryl phosphate" (hereinafter referred to as a "provitamin") as an active ingredient. The present invention also relates to a method for enhancing the immunological effects of a vaccine for viruses, bacteria and/or infectious disease pathogens by administering the composition and to a method of employing the composition.

BACKGROUND OF THE INVENTION

By virtue of the development of a vaccine or an antibiotic, humans and animals under feeding, such as cattle, pet and bleeding marine animal, have been protected from infectious diseases caused by various viruses or bacteria. In other words, the discovery of antibiotics for specific bacterial infectious diseases has already succeeded in greatly mitigating the fear of bacterial diseases. However, antibiotics or chemotherapics effective for virally infectious diseases are small in number and the predominating prophylaxis is a vaccine inoculation represented by poliomyelitis and vaccination.

Vaccines in general include an "inactivated vaccine" obtained by the inactivation of a pathogenesis virus and a "live vaccine" obtained by the attenuation thereof. Presently, examples of the vaccine practically used for humans include vaccines of poliomyelitis, measles, rubella, mumps, influenza, Japanese B encephalitis, varicella, icterus and hepatitis B. Among these, vaccines of influenza, Japanese B encephalitis and hepatitis B belong to the "inactivated vaccine" and others belong to the "live vaccine".

As compared to the inactivated vaccine, the live vaccine is generally advantageous in that immunity acquisition is close to that obtained by natural infection and the immunological effects are high. However, the live vaccine is said to have problems, such as toxicity may recover or the quality is unstable. On the other hand, the inactivated vaccine, which is lower in toxicity than the live vaccine, is not completely free of toxicity, and aggressive studies are being made with an attempt to develop more safe and effective component vaccines using genetic engineering means. However, these vaccines have some problems in practical use.

As described above, many vaccines are being used in practice; however, their prophylactic effect is not sufficiently high and various methods for enhancing the immunological effects of vaccine are being studied. For example, use of an adjuvant is one means for enhancing the effect of vaccine. A long known synthetic Freund's adjuvant has also been attempted, but this adjuvant disadvantageously causes a strong adverse reaction, having a problem in safety.

In general, when a vaccine is inoculated to an organism, the immunological effects thereof can be determined by measuring the amount of specific antibody in blood.

In the case of an antigen having hemagglutination activity, such as influenza, the amount of specific antibody in blood can be measured by hemagglutination inhibition. More specifically, 2-fold step dilution series of a virus solution are prepared, a constant amount of erythrocytes are added to each dilution and after the passing of a predetermined amount of time, the agglutination images are examined. The HA unit (HAU) of the virus is the reciprocal of the highest dilution number in a test tube showing agglutination positive. Thereafter, 2-fold step dilution series of a serum to be measured on the antibody unit are similarly prepared, an equivalent virus solution diluted to 4 HAU is added to each dilution, and the dilutions are left standing for a predetermined amount of time. To each of these solutions, a constant amount of erythrocytes are added and after the passing of a predetermined amount of time, the agglutination images are examined. The antibody unit (HI unit, HIU) of the serum is the reciprocal of the highest dilution number in a test tube showing complete agglutination inhibition.

In the case of an antigen having no hemagglutination activity, the amount of specific antibody in blood can be measured by passive hemagglutination (PHA) or the like. In this method, an antigen is previously conjugated to erythrocytes by employing tannic acid or chromium chloride and the antibody unit of antiserum is quantitated as HA unit.

As described above, with respect to the live vaccine, there is a fear of occurrence of mutation of the attenuated toxicity strain in vivo into a strongly toxic strain. In addition, with respect to the inactivated vaccine, there is a fear of a latent danger in essence such that the antigenicity is distorted during the inactivation operation and this gives rise to an unexpected adverse reaction.

Apart from this, group administration of a vaccine is being performed at present for the young. Therefore, in order to prevent the adverse reaction ascribable to the dispersion of the sensitivity in the host side, a more safe and effective vaccine is being demanded.

Furthermore, in the case of a virus which causes infection and proliferates on the surface of respiratory tract, such as influenza virus, unless the local secretory antibody (IgA antibody) of the respiratory tract is present in a sufficiently high concentration, the virus infection cannot be prevented even if the antibody concentration in blood is high. At present, subcutaneous inoculation of an inactivated vaccine is employed for the prophylaxis of influenza. Although this method is effective for increasing the antibody in blood, the IgA antibody is not increased. Accordingly, for preventing the infection not only by the influenza but also by viruses which cause infection and proliferate on the surface of respiratory tract or on the mucosa of digestive tract, it is important to increase the IgA antibody in addition to the antibody in blood.

In order to solve the above-described problems, the present inventors have made extensive investigations on a method for enhancing the immunological effects of a vaccine based on the estimation that when the immunological effects of a vaccine are enhanced, the dose can be reduced and in turn, the frequency of generation of an adverse reaction can be reduced. As a result, it has been found that the above-described problems can be overcome by using a specific provitamin, namely, a specific antioxidant provitamin in combination with a vaccine. The present invention has been accomplished based on this finding.

SUMMARY OF THE INVENTION

More specifically, the present invention provides the following embodiments.

(1) A composition for enhancing the immunological effects of a vaccine for viruses, bacteria and/or infectious disease pathogens, comprising a stable activity-type antioxidant provitamin.

(2) The composition for enhancing the immunological effects as described in (1) above, wherein the provitamin is at least one phosphoric acid ester selected from L-ascorbic acid-2-phosphate, α-tocopheryl phosphate and salts thereof.

(3) The composition for enhancing the immunological effects as described in (1) or (2) above, wherein the provitamin is selected from alkali metal salts and alkaline earth metal salts.

(4) The composition for enhancing the immunological effects as described in any one of (1) to (3) above, wherein the immunological effects of a vaccine is increased to 2 times or more in terms of the serum antibody unit.

(5) The composition for enhancing the immunological effects as described in (4) above, wherein the serum antibody unit is an antibody unit measured by hemagglutination inhibition (HAI) or passive hemagglutination (PHA).

(6) The composition for enhancing the immunological effects as described in any one of (1) to (3) above, wherein the action of enhancing immunological effects is an action of promoting the activation of macrophage.

(7) The composition for enhancing the immunological effects as described in any one of (1) to (3) above, wherein the action of enhancing the immunological effects is an action of promoting the secretory IgA induction in the respiratory tract.

(8) The composition for enhancing the immunological effects as described in any one of (1) to (7) above, which is perorally administered.

(9) The composition for enhancing the immunological effects as described in any one of (1) to (7) above, which is administered intramuscularly, intradermally, intraveneously, subcutaneously, intranasally or externally.

(10) The composition for enhancing the immunological effects as described in (8) above, which is perorally administered in a dose of 0.5 to 1,000 mg/kg per day.

(11) The composition for enhancing the immunological effects as described in any one of (1) to (7) above, which is injection administered in a dose of 0.5 to 1,000 mg/kg per day.

(12) The composition for enhancing the immunological effects as described in any one of (1) to (11) above, which is used for mammals including human, birds or fishes.

(13) The composition for enhancing the immunological effects as described in (12) above, which is used for at least one animal under high-density feeding, selected from cattle, pig, fowl, horse, poultry, pet, ornamental animal, breeding marine animal and laboratory animal.

(14) A method for enhancing the immunological effects of a vaccine for viruses, bacteria and/or infectious disease pathogens, comprising administering the composition in a pharmaceutically effective amount for enhancing the immunological effects described in any one of (1) to (13) above to a patient in need thereof.

(15) A method for employing a composition for enhancing the immunological effects, comprising blending the composition for enhancing the immunological effects described in any one of (1) to (13) above with feed, premix or drink.

(16) A method for employing a composition for enhancing the immunological effects, comprising previously mixing the composition for enhancing the immunological effects described in any one of (1) to (13) above with a vaccine and then administering the vaccine.

DESCRIPTION OF THE PREFERRED EMBODIMENTS

The present invention provides a composition for enhancing the immunological effects of a vaccine for viruses, bacteria and/or infectious disease pathogens, comprising a stable activity antioxidant provitamin.

By taking into account the fact that the provitamin exhibits excellent immunopotentiative activity when injection administered into a body and also that L-ascorbic acid phosphates as one of the provitamin exhibit antiviral activity based on the immunopotentiative activity against virus diseases, the present inventors considered that the provitamin must be effective in enhancing the prophylactic effect of a vaccine based on the sthenia of circulating antibody or cell-mediated immunity, and made investigations to use a vaccine and the provitamin in combination.

Other than provitamins, some substances exhibit the above-described immunopotentiative activity. For example, a natural substance contained in the fruit body of Grifola erondosa exhibits, when perorally administered, immunopotentiative activity (see, International Journal of Immunopharmacology, Vol. 12, No. 6, 675–684 (1990)) and also fluctuates, when perorally administered, the lymphocyte subset in blood (see, Syokaki to Meneki (Digestive Apparatus and Immunity), No. 20, pp. 78–82 (1988)). Also, an agent for enhancing the immunological effects of a vaccine for viruses and bacterial, comprising a glucan having a β-1,3-glycoside bond as a main chain and originated in a mushroom has been disclosed (see, JP-A-6-172217). As such, the effect of the combination of an immnunopotentiator perorally administered and a vaccine is already known. However, the effect of the combination of a provitamin derivative and a vaccine is not yet known at present.

As a result of investigations by the present inventors, it is recognized that when a vaccine and the provitamin are administered in combination, both the circulating antibody and the produced antibody are enhanced compared with the administration of only a vaccine. Also, the macrophage activity, as one index for the cell-mediated immunity, is enhanced. Furthermore, it is verified that even when the amount of a vaccine used is greatly reduced, the prophylactic effect obtained is sufficiently high. As a result, the above-described problems all can be overcome.

The term "provitamin" as used in the present invention means a substance which is physically stable and inactive, but expresses satisfactory vitamin activity under the action of an intercellular enzyme of the objective animal. Specifically, ascorbic acid-2-phosphates and tocopheryl phosphates can be used as the provitamin of the present invention. However, ascorbic acid-2-sulfate and the like are known to fail in exerting satisfactory activity in organisms because the organism does not have a hydrolase therefor, and therefore, these cannot be used in the present invention.

The ascorbic acid-2-phosphates for use in the present invention are represented by the following formula (1):

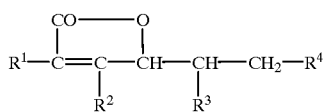

(1)

wherein $R^1$ is a group capable of bonding to the carbon at the 2-position of the ascorbic acid through a phosphoric acid ester bond and converting into a hydroxyl group in vivo, $R^2$ is a hydroxyl group or a group capable of converting into a hydroxyl group in vivo, and $R^3$ and $R^4$ each is a hydroxyl group or a hydrophobic group, provided that $R^3$ and $R^4$ are not a hydroxyl group at the same time.

$R^1$ is preferably a group containing at least one of a phosphoric acid group, a pyrophosphoric acid group, a triphosphoric acid group, a polyphosphoric acid group, a sulfuric acid group and a glycosyl group.

$R^2$ is preferably a group containing at least one of a hydroxyl group, a phosphoric acid group, a polyphosphoric acid group, a sulfuric acid group, a glycosyl group, an alkyl group, an alkenyl group and a phenyl group.

$R^3$ and $R^4$ each may be a fatty acid residue or a group containing at least one of an alkyl group, an alkenyl group and a phenyl group.

Specific examples of preferred ascorbic acid-2-phosphoric acid for use in the present invention include salts of L-ascorbic acid-2-monophosphate. The salt may be at least one salt selected from ammonium, sodium, potassium, magnesium, calcium, strontium, barium, aluminum, iron, zinc, bismuth and organic amines. Among these, alkali metal salts and alkaline earth metal salts are preferred.

In the present invention, $R^2$, $R^3$ and $R^4$ each may be a fatty acid ester having from 10 to 22 carbon atoms, preferably L-ascorbic acid-2-phosphate-6-laurate, L-ascorbic acid-2-phosphate-6-myristate, L-ascorbic acid-2-phosphate-6-palmitate, L-ascorbic acid-2-phosphate-6-stearate, L-ascorbic acid-2-phosphate-6-oleate, L-ascorbic acid-2-phosphate-6-linoleate, L-ascorbic acid-2-phosphate-6-linolenate, L-ascorbic acid-2-phosphate-6-arachidonate, L-ascorbic acid-2-phosphate-5,6-O-benzylidene, an L-ascorbic acid-2-phosphate-5,6-O-benzylidene derivative, or a salt thereof. The salt thereof may be at least one salt selected from ammonium, sodium, potassium, magnesium, calcium, strontium, barium, aluminum, iron, zinc, bismuth and organic amines.

The tocopherol in the tocopheryl phosphate and salts thereof for use in the present invention is represented by the following formula (2):

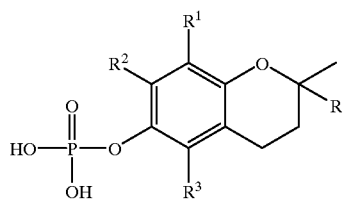

(2)

According to the substituents $R^1$, $R^2$ and $R^3$, each representing a hydrogen atom or a methyl group, this compound is known as α-tocopherol ($R^1$, $R^2$ and $R^3$: $CH_3$), β-tocopherol ($R^1$ and $R^3$: $CH_3$, $R^2$: H), γ-tocopherol ($R^2$ and $R^3$: $CH_3$, $R^1$: H), δ-tocopherol ($R^3$: $CH_3$, $R^1$ and $R^2$: H), ζ2-tocopherol ($R^1$ and $R^2$: $CH_3$, $R^3$: H) or η-tocopherol ($R^1$ and $R^3$: $CH_3$, $R^2$: H), and can be a constituent element of the compound represented by formula (1). In addition, ζ1-tocopherol and ε-tocopherol, in which, the long chain alkyl group bonded to the carbon atom adjacent to the O atom in the benzopyrane structure of α-tocopherol or β-tocopherol is displaced by the following formula (3):

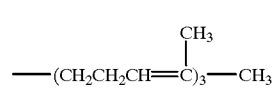

(3)

are known and either one can be a constituent element of the tocopheryl phosphate and salts thereof for use in the present invention.

Out of the tocopherol derivatives represented by formula (2) for use in the present invention, the compounds having an acidic group can be easily formed into a salt by allowing a basic compound to act thereon. Examples of the basic compound include sodium hydroxide, potassium hydroxide, calcium hydroxide, sodium carbonate and potassium hydrogencarbonate.

Examples of the salt of tocopheryl phosphate, which can be used in the present invention, include alkali metals and alkaline earth metals, such as sodium, potassium, calcium, magnesium, aluminum, zinc and lithium. Among these, sodium salt is preferred because the solubility in water is high and the toxicity is low.

The composition of the present invention can also contain a surfactant. The surfactant which can be used in the present invention may be any surfactant generally available on the market and examples thereof include phospholipid, monoglyceride, sucrose fatty acid ester, sorbitan ester of fatty acid, polyoxyethylene sorbitan ester of fatty acid and polyoxyethylene glycerin ester of fatty acid.

In order to effectively exert the immunopotentiative activity, the provitamin is preferably administered by mixing it with feed or drinking water or by a syringe. If the IgA antibody secreted on the respiratory airway or digestive tract mucosa shows no sthenia of production, the immunopotentiation of a influenza vaccine is not enhanced much because the IgA antibody plays an important role in the prophylaxis.

In the case where the provitamin is perorally administered, it is recognized that the provitamin appropriately contacts with the respiratory airway or digestive tract mucosa to stimulate the mucosa, and thereby promote the secretion of the IgA antibody. By virtue of these three mechanisms of circulating antibody, cell-mediated immunity and IgA antibody, the living body is prevented from virus infection. This effective immunopotentiative effect is estimated to occur also, for example, on the influenza vaccine. In fact, the present inventors have confirmed that when the provitamin is perorally administered, the IgA antibody shows significant enhancement in the production accompanying the administration of a Sendai virus vaccine closely related to the influenza virus and the prophylactic effect is enhanced.

In the present invention, the activity of enhancing the immunological effects of a vaccine by the provitamin is considered to result because the provitamin non-specifically activates the prophylactic mechanism of a host. The provitamin is found to have the capability of accelerating the immunological effects of any kind of vaccine and to also be widely applicable to bacteria vaccines irrespective of the kind of virus vaccine. Furthermore, this effectiveness is expected to extend even to protozoan diseases such as malaria.

In the present invention, the immunological effects of a vaccine are as high as 2 times or more in terms of the serum antibody unit. Immunological effects of less than 2 times the normal are disadvantageously insufficient as the immunological effects of the composition of the present invention. The immunological effects are preferably 4 times in terms of the serum antibody unit.

The provitamin may be administered into a body by injection administration, peroral administration or the like. The administration method may be appropriately selected according to the kind of vaccine, the condition of the host and the like. However, in view of the accelerated production of IgA antibody and the safety and ease of administration, the peroral administration is preferred over the injection administration. The provitamin may be previously mixed with a vaccine and then perorally administered.

The peroral administration is further advantageous in that the provitamin does not need to be purified to a high purity, and for example, the bacteria which produce the provitamin can be used in the form of a cell as it is or as a mixture thereof, so that the production cost can be reduced. In the present invention, the effective dose of the provitamin is, in terms of active ingredient provitamin, from 0.5 to 1,000 mg/kg, preferably from 5 to 500 mg/kg, still more preferably from 10 to 100 mg/kg, per day for peroral administration, and from 0.05 to 150 mg/kg, preferably from 0.5 to 120 mg/kg, still more preferably from 1 to 100 mg/kg, per day for injection administration. If the dose is less than this range, a sufficiently high effect cannot be obtained, whereas even if the dose exceeds the above-described range, an effect proportional to the dose cannot be obtained, which is disadvantageous in view of profitability.

A vaccine is inoculated in an usual amount within a range to assure the biological safety and effect. Usually, an attenuated virus strain is used and this strain may be administered by a method commonly used in the vaccine administration and may be inoculated perorally or using a nebulizer or syringe. Depending on the kind of virus, the amount inoculated varies, but usually, a vaccine is suitably inoculated within a range from 10 to 10,000 CIU (cell infectious unit).

With respect to the administration method, any method commonly used for vaccine inoculation may be used and examples thereof include contacting with any mucosal tissue, such as oral, nasal or bronchial mucosa, administration by nebulization, and injection such as intradermal injection.

The composition of the present invention can be blended with feed, premix or drink according to the above-described dose.

The composition for enhancing the vaccine effect of the present invention may be fed to an animal by blending it with a protein feed, a general feed such as carbohydrate feed, a feed additive or a feed ingredient. The optimal feed amount varies depending on the kind of animal, stage or eucrasia, and therefore, may be appropriately determined according to the conditions where the composition is applied.

The provitamins of the present invention can also be used in the form of a metal salt and examples of the metal constituting the metal salt include alkaline earth metals such as calcium, magnesium and barium. At least one metal selected from these alkaline earth metals is used and the metal salt of fatty acid for use in the present invention can be produced by an ordinary method, such as a method of neutralizing an oxide, a hydroxide or a carbonate of the alkaline earth metal and a fatty acid described above, or a method of double-decomposing an alkali metal salt of fatty acid by an oxide, a hydroxide or a carbonate of alkaline earth metal.

The preparation for administration to animals of the present invention is effective for mammals including humans, birds and fishes, and is particularly effective for animals under high-density feeding, such as cattle, pig, fowl, horse, poultry, pet, breeding marine animals and laboratory animals. In general, the feeding environment of the animal under high-density feeding is restricted, and therefore, the animal suffers from stress which readily causes reduction of the immunological function and is prone to viral infection. Thus, it was revealed that the composition of the present invention improves the lipid metabolism, which has an effect of preventing viral infection, which gives rise to health deterioration of a useful animal, and ameliorating the eucrasia.

EXAMPLES

The present invention is described in greater detail below by referring to the Examples, however, the present invention is not limited to these Examples. Unless indicated otherwise herein, all parts, percents, ratios and the like are by weight.

Example 1

Hereinafter, L-ascorbic acid-2-monophosphate is referred to as "A2P" and α-tocopheryl phosphate is referred to as "VEP". For example, A2P-Mg indicates a magnesium salt of L-ascorbic acid-2-monophosphate and dl-VEP-Na indicates an Na salt of dl-α-tocopheryl phosphate.

The provitamins prepared to have a composition in the following Formulation Examples 1 to 4 were individually or in combination (hereinafter referred to as "provitamin") dissolved in a phosphate buffered saline (PBS) to a concentration of 0.5% and then continuously administered perorally or peritoneally to a mouse (ICR, 3 weeks old, male) from two weeks before the administration of a vaccine. The sample was administered such that APM per day was 80 mg/kg-body weight in the case of peroral administration and the dose per day was 40 mg/kg-body weight in the case of injection.

The vaccine used here was TR-5 strain which is an attenuated strain of Sendai virus, and 500 CIU (cell infectious unit) thereof was nasally administered to a mouse under ether anesthesia. Specifically, a stock solution (106 CIU/ml) of TR-5 strain was diluted with PBS and 50 μl of each sample was nasally administered. After the administration of vaccine, the serum was sampled after various periods of time had elapsed (inoculation day, after 7 days, after 14 days and after 21 days) and the antiviral antibody unit in the serum was measured by the hemagglutination inhibition (HI) reaction which inhibits the hemagglutination (HA) reaction.

The HA reaction is a reaction where a virus particle or an HA antigen adsorbs to an erythrocyte and combines the erythrocytes with each other to cause hemagglutination. In the measurement of the HA unit, 2-fold step dilution series of a virus solution are prepared, a constant amount of erythrocytes are added to each dilution and after the passing of a predetermined time, the agglutination image is examined. The HA unit (HAU) is the reciprocal of the highest dilution number in a test tube showing agglutination positive. The HA reaction is inhibited by previously adding an antiviral antibody to the virus solution. This is the HI reaction.

The HI antibody unit (HIU) is the reciprocal of the highest dilution number of a serum which completely inhibits the HA reaction attributable to 4 HAU virus antigen.

Formulation:

|  | Formulation Example 1 | Formulation Example 2 | Formulation Example 3 | Formulation Example 4 |
|---|---|---|---|---|
| A2P-Mg | 100% |  | 40% | 30% |
| A2P-Na |  | 100% | 30% | 10% |
| A2P-Ca |  |  |  | 10% |
| A2P-K |  |  |  | 10% |
| dl-VEP-Mg |  |  |  | 10% |
| dl-VEP-Na |  |  | 30% | 10% |
| dl-VEP-Ca |  |  |  | 10% |
| dl-VEP-K |  |  |  | 10% |

Test Method:

To 25 μl of a serum subjected to 2-fold step dilution, 25 μl of a virus solution adjusted to 16 HAU was added and allowed to stand at room temperature for 1 hour. Subsequently, 50 μl of a 0.5% chicken erythrocyte suspension was added and allowed to stand at 4° C. for 1 hour. Thereafter, the HI unit was determined. The results are shown in Table 1.

TABLE 1

Effect of Provitamin on Transition of Circulating Antibody Unit After Administration of Vaccine

| HIU | (Peroral Administration) | | | | (Peritoneal Administration) | | | |
|---|---|---|---|---|---|---|---|---|
| Days Passed After Infection | 0 | 7 | 14 | 21 | 0 | 7 | 14 | 21 |
| Vaccine-free segment | <16 | <16 | <16 | <16 | <16 | <16 | <16 | <16 |
| 500 CIU vaccine | <16 | <16 | <16 | 16 | <16 | <16 | 16 | 32 |
| 500 CIU vaccine + Formulation Example 1 | <16 | <16 | 16 | 64 | <16 | 16 | 32 | 64 |
| 500 CIU vaccine + Formulation Example 2 | <16 | <16 | 16 | 64 | <16 | <16 | 32 | 64 |
| 500 CIU vaccine + Formulation Example 3 | <16 | <16 | 64 | 64 | | | | |
| 500 CIU vaccine + Formulation Example 4 | <16 | 16 | 64 | 64 | | | | |

By using a vaccine and a provitamin, the circulating antibody unit was significantly increased as compared with the case of using only the vaccine.

Example 2

The provitamin and a vaccine (500 CIU) were inoculated in the same manner as in Example 1. 14 Days after the inoculation of the vaccine, macrophages were sampled from the abdominal cavity of the mouse and the number of macrophages was counted through a microscope. Also, the activity of the macrophage was examined as follows. Fibrosarcoma SMT-5 (target cell) and the sampled macrophages (effector cell) were mixed at a ratio of 1:7 and cultured in $CO_2$ medium for 24 hours. 8 Hours before the completion of culture, $^3$H-thymidine was added and the amount of $^3$H-thymidine taken up into the residual target cells was measured by a liquid scintillation counter. From the value obtained, the activity of macrophage was determined. The amount of $^3$H-thymidine in the control group was the amount of $^3$H-thymidine taken up into the target cells where the macrophages were not added.

The results are shown in Table 2.

TABLE 2

Effect of Vaccine and Provitamin on Activation of Macrophage

| Sample | Administration Route | Macrophage/ Body (×$10^6$) | Macrophage Activity |
|---|---|---|---|
| 500 CIU vaccine | Peritoneal | 3.9 | 9.5 |
| 500 CIU vaccine + Formulation Example 1 | Peritoneal | 9.1 | 22.1 |
| 500 CIU vaccine + Formulation Example 1 | Peroral | 6.8 | 20.5 |
| 500 CIU vaccine + Formulation Example 2 | Peroral | 6.5 | 20.2 |
| 500 CIU vaccine + Formulation Example 3 | Peroral | 6.3 | 21.3 |
| 500 CIU vaccine + Formulation Example 4 | Peroral | 7.1 | 23.7 |

By using a vaccine and a provitamin in combination, the production of macrophage was enhanced and the activation was caused, as compared with the case of using only the vaccine.

Example 3

The provitamin and a vaccine were inoculated in the same manner as in Example 1. 14 Days after the inoculation of vaccine, the mouse was sacrificed, the trachea and bronchia were twice washed with 1 ml of PBS (phosphate buffered saline), and IgA recovered in the PBS was measured by the enzyme linked immunosorbent assay (ELISA).

ELISA

Sendai virus was fixed on a plate and reacted with a test solution. Thereafter, peroxidase marker anti-mouse IgA immunoglobulin was reacted and then phenylenediamine 2HCl was added to cause coloration. OD 492 was measured and from the calibration curve obtained based on the standard IgA, the IgA amount in the test solution was determined.

The results are shown together in Table 3.

TABLE 3

Effect of Provitamin on Secretory IgA Induction by Sendai Virus Live Vaccine

| Sample | Administration Route | IgA (U/μg) |
|---|---|---|
| Control group (not treated) |  | 14 |
| 500 CIU vaccine | Peritoneal | 19 |
| 500 CIU vaccine + Formulation Example 1 | Peritoneal | 69 |
| 500 CIU vaccine + Formulation Example 1 | Peroral | 51 |
| 500 CIU vaccine + Formulation Example 2 | Peroral | 69 |
| 500 CIU vaccine + Formulation Example 3 | Peroral | 68 |
| 500 CIU vaccine + Formulation Example 4 | Peroral | 70 |

By using a vaccine and a provitamin in combination, the induction of secretory IgA was enhanced, as compared with the case of using only the vaccine.

Example 4

The provitamin and a vaccine were inoculated in the same manner as in Example 1, and 14 days after the inoculation of attenuated vaccine, Sendai virus strongly toxic strain $(1.7 \times 10^7$ CIU/ml) was subjected to 15-hold dilution. Subsequently, 70 µl (about $8 \times 10^4$ CIU: 15 $LD_{50}$) of the dilution was nasally infected to a mouse under ether anesthesia and 20 days after the infection with the strongly toxic strain, the survival rate of mice was examined. The results are shown in Table 4.

(Measurement of $LD_{50}$)

The test solution was step-diluted and each dilution was used for a group of animals. The life and death were examined and the point of dilution degree where 50% of death was recognized was designated as $LD_{50}$.

TABLE 4

Effect of Provitamin on Vaccine Effect

| Sample | Administration Route | Survival Rate (number of survival mice/ number of mice tested) Amount of Vaccine Inoculated (CIU) | | |
|---|---|---|---|---|
| | | 0 | 50 | 500 |
| Control group (PBS administration) | Peritoneal | 0/10 | 0/10 | 2/10 |
| Control group (PBS administration) | Peroral | 0/10 | 0/10 | 1/10 |
| Formulation Example 1 | Peritoneal | 0/10 | 8/10 | 8/10 |
| Formulation Example 1 | Peroral | 0/10 | 9/10 | 9/10 |
| Formulation Example 2 | Peroral | 1/10 | 9/10 | 10/10 |
| Formulation Example 3 | Peroral | 1/10 | 8/10 | 10/10 |

By using a vaccine and a provitamin, the survival rate was increased as compared with the case of using only the vaccine.

The provitamin of the present invention has the following prominent characteristic features, resistant to the decomposition by a digestive enzyme in vivo, very low in the toxicity, almost free of an adverse reaction even by injection administration and completely nulled in the toxicity in the case of peroral administration. In addition, the provitamin of the present invention is converted into a natural nutrient. In addition, since the toxicity is low, the provitamin may be taken as food or animal feed and even in this case, a sufficiently high vaccine enhancing effect can be expected. In the case of using the provitamin as food or feed, purification to a high purity is not necessary but the coarse product or a culture dry product in the provitamin production can provide a sufficiently high expected effect as it is and therefore, the composition for enhancing the immunological effects of a vaccine for viruses, bacteria and/or infectious disease pathogens is useful over a wide range.

While the invention has been described in detail and with reference to specific embodiments thereof, it will be apparent to one skilled in the art that various changes and modifications can be made therein without departing from the spirit and scope thereof.

What is claimed is:

1. A method for enhancing the immunological effects of a vaccine for viruses, bacterial and/or infectious disease pathogens, comprising administering a composition comprising at least one provitamin compound selected from the group consisting of L-ascorbic acid-2-phosphate, α-tocopheryl phosphates and salts thereof in a pharmaceutically effective amount to a patient in need thereof, and administering a vaccine.

2. The method for enhancing the immunological effects of a vaccine according to claim 1, wherein the salt is an alkaline metal salt or an alkaline earth metal salt.

3. The method for enhancing the immunological effects of a vaccine according to claim 1, wherein the salt is selected from the group consisting of sodium salt, potassium salt, magnesium salt and calcium salt.

4. The method for enhancing the immunological effects of a vaccine according to claim 1, wherein the composition is administered perorally.

5. The method for enhancing the immunological effects of a vaccine according to claim 4, wherein the composition is administered in a dose of 0.5 to 1,000 mg/kg per day.

6. The method for enhancing the immunological effects of a vaccine according to claim 1, wherein the composition is administered intramuscularly, intradermally, intraveneously, subcutaneously, intranasally or externally.

7. The method for enhancing the immunological effects of a vaccine according to claim 6, wherein the composition is administered in a dose of 0.5 to 1,000 mg/kg per day.

8. The method for enhancing the immunological effects of a vaccine according to claim 1, wherein the composition is administered by providing feed, premix or drink which is blended with the composition.

9. The method for enhancing the immunological effects of a vaccine according to claim 1, wherein the composition is administered to mammals, birds or fishes.

10. The method for enhancing the immunological effects of a vaccine according to claim 1, wherein the composition is administered to humans.

11. The method for enhancing the immunological effects of a vaccine according to claim 1, wherein the composition is administered to at least one animal under high-density feeding selected from the group consisting of cattle, pig, fowl, horse, poultry, pet, ornamental animal, breeding marine animal and laboratory animal.

12. The method for enhancing the immunological effects of a vaccine according to claim 1, wherein the vaccine is a vaccine for influenza virus.

13. The method for enhancing the immunological effects of a vaccine according to claim 1, wherein the immunological effects of a vaccine is increased to 2 times or more in terms of a serum antibody unit.

14. The method for enhancing the immunological effects of a vaccine according to claim 13, wherein the serum antibody unit is an antibody unit measured by hemagglutination inhibition (HAI) or passive hemagglutination (PHA).

15. The method for enhancing the immunological effects of a vaccine according to claim 1, wherein an action of enhancing immunological effects is activation of macrophage.

16. The method for enhancing the immunological effects of a vaccine according to claim 1, wherein an action of enhancing the immunological effects is secretory IgA induction in the respiratory tract.

* * * * *